United States Patent [19]

Allen

[11] 4,240,937
[45] Dec. 23, 1980

[54] ALLOY FIBERS OF RAYON AND AN ALKALI METAL OR AMMONIUM SALT OF AN AZEOTROPIC COPOLYMER OF POLYACRYLIC ACID AND METHACRYLIC ACID HAVING IMPROVED ABSORBENCY

[75] Inventor: Thomas C. Allen, Asheville, N.C.

[73] Assignee: Akzona Incorporated, Asheville, N.C.

[21] Appl. No.: 866,797

[22] Filed: Jan. 3, 1978

Related U.S. Application Data

[63] Continuation-in-part of Ser. No. 603,483, Aug. 11, 1975, Pat. No. 4,066,584.

[51] Int. Cl.³ .................................................. C08L 1/02
[52] U.S. Cl. .......................... 260/17.4 CL; 128/284; 128/285; 128/290 R; 128/296; 260/17.4 R; 264/191
[58] Field of Search ................. 260/17.4 R, 17.4 CL; 128/284, 285, 290 R, 296

[56] References Cited

U.S. PATENT DOCUMENTS

| 3,256,372 | 6/1966 | Adams et al. | 260/17.4 |
| 3,816,357 | 6/1974 | Church | 260/17.4 |
| 4,066,584 | 1/1978 | Allen et al. | 260/17.4 CL |

FOREIGN PATENT DOCUMENTS

| 2320998 | 4/1977 | France | 260/17.4 |
| 1529493 | 10/1978 | United Kingdom | 260/17.4 |

OTHER PUBLICATIONS

Chem. Absts. vol. 86: 141533 p., Allen et al. Fibers--Rayon—Copolymers -poly(methacrylic acid).

Primary Examiner—Edward M. Woodberry
Attorney, Agent, or Firm—Francis W. Young; Jack H. Hall

[57] ABSTRACT

Cardable cellulosic fibers having improved water and fluid absorbency are made by incorporating therein an alkali metal or ammonium salt of a copolymer of acrylic acid and methacrylic acid prepared by a process wherein the two monomers are mixed together in ratios during the polymerization so that the amount of copolymer chains substantially richer in methacrylic acid moieties than the total ratio of acrylic acid and methacrylic acid monomers included in the copolymerization process and the number of copolymer chains considerably lower in degree of polymerization than the copolymer average are minimized.

18 Claims, No Drawings

ALLOY FIBERS OF RAYON AND AN ALKALI METAL OR AMMONIUM SALT OF AN AZEOTROPIC COPOLYMER OF POLYACRYLIC ACID AND METHACRYLIC ACID HAVING IMPROVED ABSORBENCY

This application is a continuation-in-part of application Ser. No. 603,483 filed Aug. 11, 1975 by David Denning and myself, now U.S. Pat. No. 4,066,584, issued Jan. 3, 1978 and relates to highly absorbent fibers, for example, viscose rayon, hydroxypropylcellulose, and hydroxyethylcellulose, made from wood pulp or other cellulosic materials, which are useful in the production of absorbent nonwoven articles such as diapers, tampons, sanitary napkins, medical sponges, soil mulches, wiping cloths, and the like. Each of these articles requires a material having a high capacity for absorbing and retaining water and other aqueous fluids, particularly, body fluids. As disclosed in my earlier filed application, cellulosic fibers have found wide use in these and similar applications because of the hydrophilic nature of the cellulose molecule and its fibrous structure which contributes integrity, form, shape, wicking ability, and liquid retention to a nonwoven material.

It has been disclosed before, for example, in U.S. patent application Ser. No. 330,378, filed Feb. 7, 1973 and assigned to the assignee of this application, now abandoned and in U.S. Pat. No. 3,844,287 that the incorporation of metal salts and ammonium salts of polyacrylic acid in regenerated cellulose fibers increases the fluid absorbency of the fibers over that of fibers produced from the same viscous solution but without the salts of the alloying polymer. Other examples of hydrophilic polymers incorporated into viscose to increase the hydrophilic properties of the fiber are carboxymethylcellulose and carboxyethyl starch as described in U.S. Pat. Nos. 3,423,167 and 3,847,636, respectively.

The parent application discloses that fibers containing copolymers of acrylic acid and methacrylic acid have certain advantages over the various homopolymers described above. These advantages are probably realized by the fact that the various comonomers offer a variety of properties necessary for the complex requirements necessary for the commercial utilization of a highly absorbent fiber in sophisticated formed products for a specific end use. For example, in the parent application, it is believed that the methacrylic acid units impart stiffness to the polymer chain, resulting in the observed improved absorbency and fiber processing due to increased fiber cohesion properties.

It is an object of this invention to improve the fluid absorbency of rayon fibers.

Another object of the invention is to provide a process for making rayon fibers of improved absorbency which can be carded and otherwise processed on available apparatus and are adapted for making the absorbent articles listed above.

The foregoing objects and others are accomplished in accordance with this invention, generally speaking, by providing a process for making rayon fibers containing as an alloying material a copolymer of acrylic acid and methacrylic acid which has been prepared by a copolymerizing process wherein the addition of the two monomers is controlled so that the amount of copolymer chains which are substantially richer in methacrylic acid moieties than the total ratio of acrylic acid and methacrylic acid monomers included in the copolymerization process and the number of copolymer chains considerably lower in degree of polymerization than the copolymer average are minimized. For example, if a 50/50 copolymer of acrylic acid and methacrylic acid is included in the rayon fiber, the copolymer is prepared by a process wherein the amount of each monomer at the beginning of the polymerization and the addition of more of each monomer to the polymerizing mixture are controlled so that the ratio of the acrylic acid and methacrylic acid moieties is substantially the same as the total ratio of acrylic acid and methacrylic acid monomers included in the copolymerization process. Various methods for copolymerizing acrylic acid and methacrylic acid to make the copolymer contemplated for use in practicing my invention described in the aforesaid application Ser. No. 603,483 are described in that application. One of these methods involves controlled monomer addition. My continued research has now established that copolymers produced in this way when included in rayon fibers especially at higher concentrations, i.e. from about 10 to 40 percent CIV, improve the fluid absorbing of the fiber more per unit weight of copolymer than copolymers of acrylic and methacrylic acids produced by adding all of the comonomers at the beginning of the copolymerization process. As disclosed in my earlier application, 50/50 acrylic acidmethacrylic acid copolymers are preferred but copolymers prepared in ratios of from 90 mole acrylic acid and 10 mole methacrylic acid to ratios of 10 mole acrylic acid to 90 mole methacrylic acid may be used as alloying materials in practicing the invention provided the monomer addition is controlled so that the ratio of the acrylic acid and methacrylic acid moieties in substantially all of the copolymer chains is substantially the same as the total ratio of acrylic acid and methacrylic acid monomers included in the copolymerization process.

It has now been found that when using copolymers of acrylic acid and methacrylic acid made by adding all of the monomers at the beginning of the copolymerization process, the increase in absorbency obtained by adding more copolymer to the fiber levels off at a certain point. This point will vary with the ratio of acrylic acid to methacrylic acid and with the molecular weight of the copolymer.

It is well known in basic copolymerization theory that due to different rates of reactivity of the different comonomers with either of the terminal free radical species, the commonomers will not enter the copolymer chains in the same ratio as their molar composition in the monomer mixture. Therefore, the 50/50 by weight copolymer of acrylic acid and methacrylic acid in Example 3 of the parent application may have the equal amount weightwise of the two comonomers averaged among all the copolymer chains, but the individual chains will vary greatly in regard to monomer composition.

The exact accepted method of variation can be calculated from known equations. The data necessary for such calculations are the molar fractions of the two monomers and their reactivity ratios. The reactivity ratios can be found in the literature for a number of monomer combinations. These values were determined experimentally, but since the acrylic acidmethacrylic acid combination is not common, the reactivity ratios were estimated from the Price-Alfrey Q and e parameters. Table I shows a computer program output of instantaneous concentrations of acrylic acid in the feed and the copolymer for the system of 50/50 weight/weight of acrylic acid and methacrylic acid. Note that only 40 molar percent of the copolymer chains contain between 60/40 and 40/60 weight percent of acrylic to methacrylic acid, a reasonable bracket for the desired 50/50 ratio. In the second part of Table I it is seen that starting with a 65/35 weight ratio of acrylic to methacrylic acid produces roughly a 50/50 weight ratio of the two monomers up until about 40 percent weight cohesion. Past this point, the methacrylic acid monomer has been depleted so that the chains now become increasingly richer in acrylic acid.

As shown in Table I, the methacrylic acid moieties tend to enter the chains faster than the acrylic acid moieties so that the ratio of acrylic acid to methacrylic acid in the monomer supply tends to drift in favor of acrylic acid. There are several possible ways to control the monomer addition so that the amounts of acrylic acid to methacrylic acid in the monomer supply stays at the desired ratio. The preferred method is to begin the polymerization with a monomer supply richer in acrylic acid so that the ratio of the two monomers is greater than that desired in the copolymer. The withheld methacrylic acid is then added later in the polymerization to compensate for the drift in favor of acrylic acid in the monomer feed. The exact procedure for controlling the monomer addition must be worked out by experiment by one skilled in the art depending on the time and temperature of polymerization, the initiator type and amount, and the particular equipment used in the polymerization process. However, a starting point can be obtained by using basic copolymerization theory. For example, as shown in Table IB, a 65/35 weight ratio of acrylic acid to methacrylic acid produces an approximate 50/50 weight ratio of the two monomers in the copolymer until the drift in monomer composition changes the ratio. Therefore, in order to obtain an approximate 50/50 weight ratio copolymer of acrylic acid and methacrylic acid among all polymer chains, an initial charge of 65/35 weight ratios of monomer can be made. After the polymerization is 25 to 35 percent complete, the monomer ratio is then adjusted back from about 70/30 to the 65/35 ratio. After about 50 and 75 percent conversion of monomer to polymer, further adjustments back to the 65/35 ratio are made.

Another property of polymers that is an average among all polymer chains and will usually vary greatly is degree of polymerization (D.P.). It has been found that the same factors that tend to cause wide variations in monomer unti composition among the copolymer chains also causes wide variations in the degree of polymerization among the copolymer chains. It is believed that controlling the monomer addition during the polymerization process also gives a more narrow distribution of degree of polymerization among polymer chains. Lower molecular weight polymer chains not only tend to come out of the fiber more in the spinbath and fiber purification process, causing pollution and economy efficiency problems, and in actual use such as in a tampon in the human body, causing possible tissue irritation, but there is also evidence that lower D.P. molecular polymer chains cause lower absorbency when the fiber is in tampon form. Increasing the average degree of polymerization greatly will decrease the amount of lower D.P. material but a significant increase in viscosity will result. Although there is no known upper limit to the degree of polymerization of polymer chains in regard to this invention, the viscosity may be too high for practical handling of the polymer is regard to pumping for injection into the viscose and transfer from the polymerization vessel. It is believed that controlling the monomer addition in the copolymerization of acrylic and methacrylic acid also reduces the amount of lower molecular weight material, giving added benefits in regard to economy, toxicology, pollution, and absorbency.

TABLE I

INSTANTANEOUS COMPOSITION OF ACRYLIC ACID IN COMONOMER FEED AND COPOLYMER FROM V.E. MAYER AND R.K.S. CHAN, POLYMER PREPRINTS 8 (1), 209–215, AMERICAN CHEMICAL SOCIETY, 1967.

A. 50/50 WEIGHT/WEIGHT ACRYLIC ACID AND METHACRYLIC ACID $M_1$ = Acrylic acid  $M_2$ = Methacrylic acid
$r_1 = 0.448$  $r_2 = 2.20$
$[M_1] = 0.554$ = Molar Fraction of $M_1$  $[M_2] = 0.456$

| WEIGHT CONVERSION (percent) | $M_1/M_2$ IN COPOLYMER (weight percent) | $M_1/M_2$ IN MONOMER FEED (weight percent) |
|---|---|---|
| 0 | 32/68 | 50/50 |
| 9 | 35/65 | 53/47 |
| 34 | 40/60 | 58/42 |
| 47 | 45/55 | 63/37 |
| 56 | 50/50 | 67/33 |
| 65 | 55/45 | 71/29 |
| 71 | 60/40 | 75/25 |
| 78 | 70/30 | 80/20 |
| 83 | 75/25 | 84/16 |
| 85 | 80/20 | 86/14 |
| 91 | 90/10 | 91/9 |

B. 65/35 WEIGHT/WEIGHT ACRYLIC ACID AND METHACRYLIC ACID $M_1$ = Acrylic acid  $M_2$ = Methacrylic acid
$r_1 = 0.448$  $r_2 = 2.20$
$[M_1] = 0.69$  $[M_2] = 0.31$

| WEIGHT CONVERSION (percent) | $M_1/M_2$ IN COPOLYMER (weight percent) | $M_1/M_2$ IN MONOMER FEED (weight percent) |
|---|---|---|
| 0 | 47/53 | 65/35 |
| 49 | 48/52 | 66/34 |
| 14 | 51/49 | 68/32 |
| 30 | 55/45 | 72/28 |
| 44 | 61/39 | 75/25 |
| 53 | 65/35 | 78/22 |
| 61 | 69/31 | 80/20 |
| 71 | 76/24 | 85/15 |
| 78 | 81/19 | 88/12 |
| 82 | 84/16 | 90/10 |
| 89 | 90/10 | 92/8 |
| 94 | 94/6 | 94/6 |

The fibers of the invention can be prepared by adding, at any stage of viscose aging, but preferably by injecting into a fully ripened viscose solution, any suitable amount of the contemplated copolymer but preferably by injecting from about 2% to about 40% by weight of the copolymer into the viscose solution, based on the weight of cellulose in the viscose solution (hereinafter all percentages are given on this basis and referred to as CIV). A range of 10–20% CIV is preferred, based on a balance between increasing absorbency, economic factors, and processing conditions. The viscose solution containing the copolymer is spun or extruded through spinneret openings into an acid bath where the cellulose fiber is regenerated. The regenerated fiber is stretched in air from 0–100%, or even higher, if desired, preferably from about 30 to 50% and then run through a hot aqueous bath which can be maintained at a temperature of from ambient to 100° C., preferably from 90° C. to 97° C. The hot aqueous bath may contain various amounts of dilute sulfuric acid, sodium sulfate, and zinc sulfate. The fiber is subjected to a second stretching of from 0 to 100% in the hot bath. The total stretch in both steps is preferably in the range of 50-70%. The stretching, as is well known, imparts the necessary strength to the finished fiber. The fibers, now a large bundle of continuous filaments or tow, from the combined output of a number of spinnerets is cut into short fibers of any desired length and washed and dried to a moisture content of around 11% and baled.

After the fiber is regenerated, the copolymer occluded in the fiber will be in acid form. The copolymer must be in the form of the alkali metal or ammonium salt in order to achieve the highest degree of absorbency. The copolymer of acrylic acid and methacrylic acid may be converted to the salt form during an alkaline sodium sulfide wash bath which is conventionally used to remove metal and sulfur impurities. In some instances, it may be desirable, particularly, if an acid wash follows the sulfide, to treat the fiber with a base such as a dilute solution of sodium bicarbonate, sodium hydroxide, and the like, to complete the conversion, and insure that a high percentage of the copolymer is in the salt form. It may be necessary to limit the amount of conversion to the salt form for certain applications where the material may come into contact with the body, since a pH which is much higher than 7 to 7.5 can cause irritation of delicate membranes and serves to promote the growth of harmful microorganisms. Finally, a conventional finish, such as a surfactant, may be applied and the staple fiber may be dried in a continuous drier to a predetermined moisture content suited to the particular end use of the fiber.

The dried fiber may be baled or carded for processing into one of the final products mentioned previously. A particularly suitable use for the fiber of the invention is for tampons, which may be made, for example, by one of the methods referred to in U.S. Pat. No. 3,699,965, or by other well-known methods.

The copolymers of the invention may be prepared by any method which will produce a uniform arrangement of the monomer moieties among the polymer chains as contemplated by this invention. For example, copolymers may be prepared by adding the proper weight ratio of the two monomers to a water solution at the beginning of the polymerization. As discussed above, due to different rates of polymerization among monomers, two different comonomers will not enter a growing polymer chain in equal amounts. Therefore, the 50/50 copolymer of acrylic acid and methacrylic acid may have an equal amount weightwise of the two comonomers averaged among all the copolymer chains, but the individual copolymer chains will vary greatly in regard to monomer composition. The individual chains may vary in composition from a range of very rich in methacrylic acid to very rich in acrylic acid. It might be thought that acrylic acid will be depleted from a monomer mixture at a faster rate than methacrylic acid since the rate of polymerization of acrylates is generally about ten times greater than that of the methacrylates. However, in copolymerization the rate of polymerization is not the controlling factor in determining how a monomer will enter a growing polymer chain. For this reason, it is necessary to maintain a proper ratio of monomers throughout the polymerization. It has been found that in copolymerization of acrylic acid and methacrylic acid, both the acrylic acid moieties and the methacrylic acid moieties tend to polymerize with methacrylic acid moieties in preference to acrylic acid moieties. Hence, there is a tendency for that part of the chain first formed to contain a preponderance of methacrylic moieties leaving excess acrylic acid moieties for polymerization at the terminal end of the chain. This may be avoided by withholding some of the methacrylic acid until near the end of the polymerization so it will not be used up too early in the polymerization.

The absorbency of the fibers can be determined by various test methods. One common measure of absorbency is the Water Retention Value or Secondary Swelling ("Q") which is determined in the manner disclosed in Ser. No. 330,378 referred to above and is hereby incorporated by reference. Briefly, the test measures the amount of water retained by the fiber after centrifuging for 15 minutes at 2500-3000 times gravity from which the percentage of water retained in the sample is calculated (based on dry weight by the fiber sample). A more recent test which correlates well with actual end use evaluations has been developed. As disclosed in the parent application, the so-called Demand Wettability Test (Lichstein, Bernard, International Nonwovens and Disposables Association, 2nd Annual Symposium on Non-Woven Product Development, Mar. 5-6, 1974, Washington, D.C.), uses a novel apparatus which allows the measure of volume and rate of absorption of a fluid by maintaining the absorbent material at a zero hydrostatic head so that wetting occurs purely on demand by the absorbent material. Thus, the absorption of liquid occurs only by virtue of the ability of the absorbent material to imbibe liquid with the flow of liquid abruptly stopping at the point of saturation. Variations in the method can be made to allow for end product simulation, e.g., the fibrous mass can be compressed to simulate a tampon. Testing of the compressed fiber can then be conducted on the apparatus using a variety of external pressures and testing fluids. A third method which involves actual formation of tampons is described by G. W. Rapp in a paper "A Comparison of The Absorptive Efficiency of the Commercial Tampons" published June 1958, by the Department of Research, Loyola University, Chicago, Illinois and in the parent application.

In order to describe the invention in greater detail, embodiments thereof are described in the following examples:

EXAMPLE I

A. A solution of a 50/50 copolymer of acrylic acid and methacrylic acid wherein substantially all copolymer chains contain substantially equal amounts of acrylic acid and methacrylic acid moieties is partially neutralized with sodium hydroxide to a pH of about 5.2 and injected into a viscose solution at a concentration of about 15% CIV, thoroughly mixed with the viscose and spun into a conventional acid spinbath containing about 5% sulfuric acid, about 20% sodium sulfate, about 1% zinc sulfate and about 25 ppm lauryl pyridinium chloride at 56°-58° C. to coagulate and regenerate the cellulose to give a 22,488 denier fiber tow containing 7,496 filaments. The resulting tow is stretched 40% in air, run through a second bath at 92°-97° C. containing 3.2% sulfuric acid and about 6.15% total salts ($NaSO_4 + ZnSO_4$) and stretched 18% in the bath. The tow is then cut into 1-9/16" staple fiber lengths. The staple is washed with water, then with 0.30% sodium sulfide solution, followed with water, then with a 0.175% sulfuric acid solution, followed with water, and then followed by a 0.20% sodium bicarbonate wash. A finish solution consisting of 0.30% aqueous solution of ethoxylated sorbitan monolaurate is applied before the fibers are dried for about ½ hour in a continuous oven set at about 80° C., for about ½ hour at about 70° C., and for about another ½ hour at about 50° C. The final moisture content is about 11%.

B. The process of Example IA is repeated to prepare a fiber containing a 50/50 copolymer of acrylic acid and methacrylic acid wherein the ratio of acrylic acid and methacrylic acid moieties among the copolymer chains varies widely from the average 50/50 weight ratio as predicated in Table IA. Samples of fibers produced by the process of Examples IA and IB were transmitted to an established tampon which performed its usual syngyna absorbency tests and reported the results back. These results were obtained with a test liquid of 60 parts by volume of human blood and 40 parts by volume water and are shown in Table II.

TABLE II

| | Fiber pH (water) | Syngyna Absorbency (g/g) | Brookfield Viscosity of Copolymer (Spindle No. 2) |
|---|---|---|---|
| Example IA | 8.0 | 6.2 | 2900 |
| Example IB | 7.7 | 5.6 | 95 |

EXAMPLE II

Example IA is repeated with a 50/50 by weight copolymer produced by withholding a portion of methacrylic acid from the initial monomer charge and adding the withheld methacrylic acid incrementally throughout the polymerization process. This polymerization procedure produces a copolymer with the monomer moieties distributed as in Example IA. The fiber is carded into a fiber pad, from which discs are made by compressing and heating one gram of these fibers in a one-inch diameter tube. Samples of these discs were tested in the Demand Wettability Test using about 0.2 psi external weight and a 1% sodium chloride solution as the test fluid. The results of this evaluation are shown in Table III.

EXAMPLE III

Example IB is repeated with a 50/50 by weight copolymer produced by adding all of the monomers at the beginning of the polymerization. This polymerization procedure produces a copolymer with the monomer moieties distributed as in Example IB. The fiber is then carded, compressed, and evaluated for absorbency as in Example II. The results of this evaluation are shown in Table III.

EXAMPLE IV

The copolymer from Example III is air-dried to remove the water, extracted at ambient temperature with methyl alcohol to remove polymer chains very rich in methacrylic acid and of lower degree of polymerization. The extracted copolymer is then redissolved in water and incorporated into fiber as in Example IA. The fiber is then carded, compressed, and evaluated for absorbency as in Example II. The results of this evaluation are shown in Table III.

TABLE III

| | Fiber pH (water) | Demand Wettability (g/g) | Brookfield Viscosity (Spindle #2) (cps) |
|---|---|---|---|
| Example II | 7.3 | 6.6 | 1900 |
| Example III | 7.4 | 5.9 | 1925 |
| Example IV | 7.4 | 6.4 | 290 |

EXAMPLE V

Example II is repeated except on a larger scale staple fiber machine. The fibers are then sent to the tampon manufacturer and tested for absorbency as in Example IA. The results of this evaluation are shown in Table IV.

EXAMPLE VI

Example III is repeated except on a larger scale staple fiber machine. The fibers are tested as in Example V. The results of this evaluation are shown in Table IV.

EXAMPLE VII

Example VI is repeated except that a homopolymer of acrylic acid is used in place of a copolymer of acrylic acid and methacrylic acid. The results of this evaluation are shown in Table IV.

EXAMPLE VIII

Example VI is repeated except that a 65/35 by weight copolymer of acrylic acid and methacrylic acid was substituted for the 50/50 copolymer. The copolymer of this example was made by the continuous addition of the monomer mixture throughout the polymerization process. The results of this evaluation are shown in Table IV.

TABLE IV

| POLYMER USED | FIBER pH WATER | SALINE | POLYMER CONTENT IN FIBER (%) | WATER RETENTION VALUES | SYNGYNA ABSORBENCY 9 gms/gm |
|---|---|---|---|---|---|
| Example V | 8.2 | 5.9 | 7.6 | 1.51 | 6.3 |
| Example VI | 8.7 | 6.1 | 8.0 | 1.83 | 7.4 |
| Example VII | 8.4 | 5.8 | 7.0 | 2.01 | 7.1 |
| Example VIII | 8.5 | 5.8 | 8.5 | 1.84 | 7.1 |

The copolymer contemplated by the invention is an azeotropic copolymer of acrylic acid and methacrylic acid of the kind described in "Encyclopedia of Polymer Science and Technology", Volume 4, pages 165 and 166, published by John Wiley & Sons, Inc., New York, New York, in 1965.

Although the invention has been described in detail for the purpose of illustration, it is to be understood that such detail in solely for that purpose and that variations can be made therein by those skilled in the art without departing from the spirit and scope of the invention except as it may be limited by the claims.

What is claimed is:

1. A highly absorbent cellulosic fiber having incorporated into the cellulosic structure an alkali metal or ammonium salt of an azotropic copolymer of acrylic acid and methacrylic acid in a weight ratio of from about 10:90 to about 90:10.

2. The fiber of claim 1 wherein the cellulosic fiber is regenerated from a viscose solution and the copolymer is incorporated into the viscose solution in an amount ranging from about 2 to about 30% by weight based on the weight of cellulose in the viscose solution.

3. An article of manufacture comprising highly absorbent fibers comprising a matrix of regenerated cellulose and an alkali metal or ammonium salt of an azeotropic copolymer of acrylic acid and methacrylic acid ratio of from about 10:90 to about 90:10, respectively.

4. The article of claim 3 wherein the cellulose is regenerated from a viscose solution and the copolymer is incorporated into the regenerated cellulose in an amount ranging from about 2 to about 30% by weight, based on the weight of cellulose in the viscose solution.

5. A highly absorbent cellulosic fiber regenerated from a viscose solution containing from about 2% to about 30% by weight of an alkali metal salt or ammonium salt of an azeotropic copolymer of acrylic acid and methacrylic acid, based on the weight of cellulose in the viscose solution, the ratio of acrylic acid moieties to methacrylic acid moities in the copolymer being from about 10:90 to about 90:10 by weight.

6. The fiber of claim 5 wherein the weight ratio is about 50:50.

7. The fiber of claim 5 which is cardable.

8. An article of manufacture comprising highly absorbent fibers comprising a matrix of regenerated cellulose and an alkali metal salt or ammonium salt of an azeotropic copolymer of acrylic acid and methacrylic acid, said cellulose having been regenerated from a viscose solution containing said salt, the ratio of acrylic acid moities to methacrylic acid moieties in the copolymer in the viscose solution ranging from 10:90 to 90:10, respectively.

9. The article of claim 8 wherein the weight ratio is about 50:50.

10. The article of claim 9 in the form of a tampon.

11. A process for making a cellulosic fiber having improved water and fluid absorbency which comprises spinning a viscose solution containing an alkali metal salt or ammonium salt of an azeotropic copolymer of acrylic acid and methacrylic acid having a weight ratio of acrylic acid to methacrylic acid from about 90 to 10 mole percent to about 10 to 90 mole percent, and which copolymer has been prepared by a process wherein the addition of each of the two acid monomers is controlled throughout the copolymerization process whereby the ratios of acrylic acid moieties and methacrylic acid moieties in the copolymer chains are substantially the same as the ratios of the total of said acid monomers included in the copolymerization process.

12. The process of claim 11 wherein the amount of each of said acids at the beginning of the copolymerization and the addition of each of the two acids is controlled during copolymerization whereby the resulting copolymer chains which are substantially richer in methacrylic acid moieties than the copolymerization mixture are minimized.

13. The process of claim 11 wherein the addition of each of the two acids is controlled throughout the process in ratios whereby the number of copolymer chains which are substantially lower in degree of polymerization than the average degree of polymerization of the copolymer are also minimized.

14. The process of claim 11, 12 or 13 wherein the resulting copolymer is an approximate 50/50 copolymer.

15. The process of claim 11 wherein the copolymerizing mixture at the beginning of the copolymerization is richer in acrylic acid than in methacrylic acid.

16. The process of claim 11 wherein from about 2% to about 40% by weight of the copolymer based on the weight of cellulose in the viscose solution is injected into the viscose solution prior to spinning and the resulting mixture is spun into an acid bath where the cellulose in the resulting filament is regenerated, the resulting fiber is stretched in air from 0% to more than 100%, submerged in a hot aqueous bath, stretched from 0% to 100% in the bath, cut into short fibers, washed and dried.

17. The process of claim 16 wherein prior to drying, the regenerated fiber is submerged in an aqueous bath containing an alkali metal or ammonium base to convert the included copolymer to an alkali metal or ammonium salt.

18. A process for making a cardable cellulosic fiber having improved water and fluid absorbency which comprises spinning a viscose solution containing an alkali metal salt or an ammonium salt of an azeotropic copolymer of acrylic acid and methacrylic acid which copolymer contains from 90 to 10 mole percent acrylic acid moieties to 10 to 90 mole percent methacrylic acid moieties and has been prepared by a process wherein the addition of each of the two acids is controlled throughout the copolymerization process whereby the ratios of acrylic acid moieties and methacrylic acid moieties in the copolymer chains are substantially the same as the ratios of the total of said acid monomers included in the copolymerization process.

* * * * *

UNITED STATES PATENT AND TRADEMARK OFFICE
CERTIFICATE OF CORRECTION

PATENT NO. : 4,240,937
DATED : December 23, 1980
INVENTOR(S) : Thomas C. Allen

It is certified that error appears in the above—identified patent and that said Letters Patent is hereby corrected as shown below:

In Column 8, line 23 change "II" to --III--;

line 30 change "III" to --II--;

line 35 change "VI" to --V--.

Signed and Sealed this

Twenty-fifth Day of October 1983

[SEAL]

Attest:

GERALD J. MOSSINGHOFF

Attesting Officer   Commissioner of Patents and Trademarks